United States Patent [19]

Fawzi

[11] 4,346,220
[45] Aug. 24, 1982

[54] 1,2,4-TRIAZIN-5-ONES

[75] Inventor: Maged M. Fawzi, Wilmington, Del.

[73] Assignee: E. I. Du Pont de Nemours and Company, Wilmington, Del.

[21] Appl. No.: 526,261

[22] Filed: Nov. 22, 1974

Related U.S. Application Data

[63] Continuation of Ser. No. 597,836, Nov. 28, 1966, Pat. No. 3,905,801.

[51] Int. Cl.$^3$ .................... C07D 253/06; A01N 43/64
[52] U.S. Cl. ......................................... 544/182; 71/93
[58] Field of Search .................. 260/248 AS; 544/182

[56] References Cited

U.S. PATENT DOCUMENTS

| | | | |
|---|---|---|---|
| 3,544,570 | 12/1970 | Timmler et al. | 260/249.5 |
| 3,671,523 | 6/1972 | Westphal et al. | 544/182 |
| 3,905,801 | 9/1975 | Fawzi | 544/182 X |
| 3,961,936 | 6/1976 | Westphal et al. | 544/182 X |
| 4,036,632 | 7/1977 | Westphal et al. | 544/182 X |
| 4,252,944 | 2/1981 | Wiley | 544/182 |
| 4,309,538 | 1/1982 | Schmidt et al. | 544/182 |
| 4,315,094 | 2/1982 | Boase et al. | 544/182 |

FOREIGN PATENT DOCUMENTS

| | | |
|---|---|---|
| 2003144 | 7/1971 | Fed. Rep. of Germany . |
| 1519180 | 3/1968 | France . |

OTHER PUBLICATIONS

Draber et al., *Naturwissenschaften*, vol. 55, p. 446; CA:69:93753k.
Zauer et al., *Period. Polytech., Chem. Eng.* (Budapest), vol. 12, pp. 259–275 (1968); CA 71:124385a.
Von Stryk, *J. Chromatogr.*, vol. 56, pp. 345–348 (1971), CA:74:123874y.
Fricke., *Proc. Northeast. Weed Sci. Soc.*, vol. 25, pp. 187–192 (1971), CA 74: 139792f.
Bayer, *Proc. Northeast Weed Sci., Soc.*, vol. 25, pp.181–185 (1971), CA 74:139853b.
Murphy et al., *Proc. Northeast. Weed Sci. Soc.*, vol. 25, pp. 204–211 (1971); CA 74: 139855.
Burgis, *Proc. S. Weed Sci. Soc.*, vol. 24, pp. 198–205 (1971); CA 75: 97569b.
Draber et al., *Pestic Chem., Proc. Int. Congr. Pestic. Chem*, 2nd Ed., vol. 5, pp. 153–175 (1972); CA 80:67292s.
Lavergne et al., *J. Heterocyclic Chem.*, vol. 12, pp. 1095–1101 (1975), CA 84:121788f.
Bartl et al., *Z. Naturforsch. B:Anorg Chem., Org. Chem.*, vol. 31B, pp. 1122–1126 (1976); CA 86:88753g.
Parlar et al., *Chemospher*, vol. 8, pp. 797–807 (1979); CA 92:105167n.
Baumann., *Chemosphere*, vol. 8, pp. 869–872 (1979); CA 92:198363.
Dornow et al., *Chem. Ber.*, vol. 97, pp. 2173–2178 (1964).

*Primary Examiner*—John M. Ford

[57] ABSTRACT

Novel substituted 1,2,4-triazine-5-one which possess herbicidal properties.

6 Claims, No Drawings

1,2,4-TRIAZIN-5-ONES

RELATED APPLICATION

This application is a continuation of my earlier filed application U.S. Ser. No. 597,836, filed Nov. 28, 1966 now U.S. Pat. No. 3,905,801 for Herbicidal Compositions and Methods.

This invention relates to substituted 4-amino-3-thio-as-triazin-5(4H)-ones and to their use in herbicidal compositions and methods.

More particularly, this invention is directed to methods for the control of undesired vegetation by applying to a locus to be protected a herbicidal amount of a substituted 4-amino-3-thio-as-triazin-5(4H)-one characterized by the formula

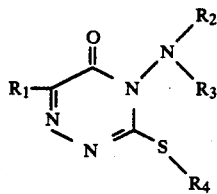

(1)

wherein
  $R_1$ is hydrogen,
  alkyl of 1 through 8 carbon atoms,
  naphthyl,
  benzyl,
  phenyl, or

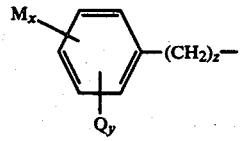

(2)

wherein
  M and Q are each separately halogen,
  nitro,
  cyano,
  alkyl of 1 through 3 carbon atoms, or
  alkoxy of 1 through 3 carbon atoms,
  x and y are each integers from 0 to 2 provided that the sum of x and y is either 1 or 2, and
  z is 0 or 1;
  $R_2$ and $R_3$ are each separately hydrogen,
  alkyl of 1 through 4 carbon atoms,
  phenyl,
  or $R_2$, $R_3$ and the nitrogen atom to which they are bonded taken together form morpholino, piperidino or pyrrolidino; and
  $R_4$ is alkyl of 1 through 4 carbon atoms,
  benzyl,
  allyl,
  carboalkoxy of 2 through 4 carbon atoms, or
  carboalkoxy alkyl of 3 through 4 carbon atoms.

While any of the compounds of Formula (1) can be used in the methods of this invention, it is preferred that $R_1$ be phenyl or benzyl or an optionally substituted phenyl or benzyl group of Formula (2) above, $R_2$ and $R_3$ each be hydrogen and $R_4$ be an alkyl of 1 through 4 carbon atoms.

The most preferred compounds of Formula (1) used in the methods of this invention are 4-amino-3-methylthio-6-phenyl-as-triazin-5(4H)-one, 4-amino-6-(p-methoxyphenyl)-3-methylthio-as-triazin-5(4H)-one, 4-amino-6-(2-methoxy-p-tolyl)-3-methylthio-as-triazin-5(4H)-one, and 4-amino-3-methylthio-6-(o-nitrobenzyl)-as-triazin-5(4H)-one.

PREPARATION

The compounds of Formula (1) are conveniently prepared according to the method set forth in Ber., 97, 2173 (1964) by heating an equimolar mixture of a thiocarbohydrazide and an α-keto or α-thioketo acid in an appropriate solvent until the reaction is complete, followed by alkylation of the resulting 4-amino-2,3-dihydro-3-thio-as-triazin-5(4H)-one. This preparative method can be more fully understood by reference to the following series of reactions wherein $R_1$, $R_2$, $R_3$ and $R_4$ have the same significance as in Formula (1), X is oxygen or sulfur and Y is halogen:

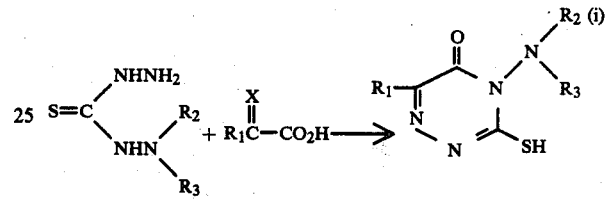

(i)

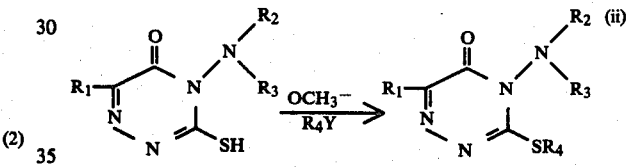

(ii)

Compounds of Formula (1) in which $R_1$ has no α hydrogen atoms are more conveniently prepared from α-keto acids than from α-thioketo acids. Compounds of Formula (1) in which $R_1$ has one or two α hydrogen atoms are prepared with equal convenience using either α-keto or α-thioketo acids.

The thiocarbohydrazides utilized as described above are prepared by reacting hydrazines and alkyldithiocarbazates as described in J.O.C., 19, 733 (1954). This method is illustrated by the following reaction:

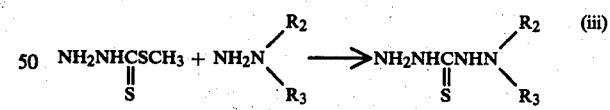

(iii)

The α-keto acids can be prepared by a variety of known methods which are outlined by Julia and Baillarge in *Bull. Soc. Chimique de France*, 850 (1959). These methods are illustrated by the following series of reactions:

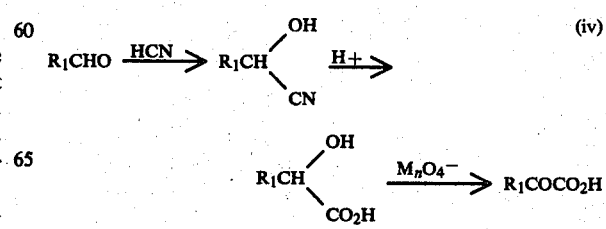

(iv)

-continued

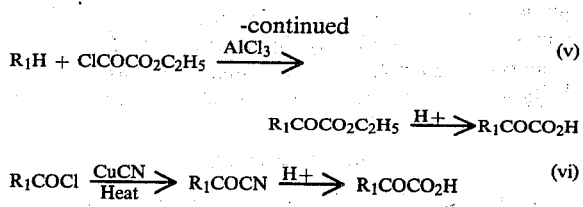

$$R_1COCl \xrightarrow[\text{Heat}]{\text{CuCN}} R_1COCN \xrightarrow{H+} R_1COCO_2H \quad \text{(vi)}$$

The α-thioketo acids having two β hydrogen atoms are prepared by condensation of the appropriate aldehyde with rhodanine in the presence of acetic acid and sodium acetate followed by alkaline hydrolysis of the resulting 5-(substituted methylene)-2-thiono-4-thiazalidinone. The conditions used are those reported in J.O.C., 15, 81 (1950). This method is illustrated by the following reaction wherein $R_1CHO$ represents an alkylaldehyde of 1 through 8 carbon atoms, benzaldehyde or optionally substituted benzaldehyde:

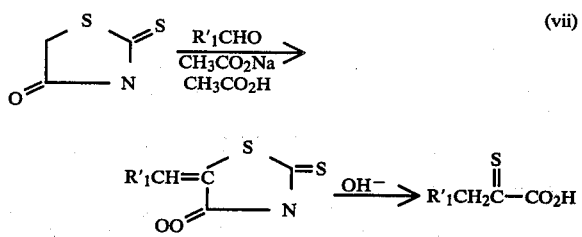

The α-thioketo acids having one β hydrogen atom can be prepared by substituting a dialkylketone of 1 through 8 carbon atoms for the aldehyde in reaction (vii) above as reported in J. Gen. Chem. (U.S.S.R.) 20, 1687 (1950), English Translation.

The compounds of Formula 1 possess excellent herbicidal activity against a wide spectrum of annual monocotyledonous and dicotyledonous weeds when applied as pre-emergent or early post-emergent treatments. These compounds are also effective for the control of perennial noxious weeds such as quackgrass and nutsedge and can be utilized either as selective herbicides in various crops or as general purpose soil sterilants for the control of unwanted vegetation over an extended period of time. An optimum level of herbicial activity is obtained when these compounds are applied to light-textured soils.

COMPOSITIONS

Compositions suitable for field application will include one or more compound of Formula (1) and such surface active agents, solid or liquid diluents, solvents and other ingredients as desired to produce wettable powder concentrates, wettable powders, dusts, aqueous suspensions, non-aqueous liquid compositions, granules, pellets and the like.

The surface active agents, or surfactants as they are often called, can be wetting, dispersing or emulsifying agents. They are generally used as wetting agents for wettable powders and dusts, as dispersing agents for wettable powders and aqueous or oil dispersions and as emulsifying agents for emulsifiable concentrates. The surfactants can include many anionic, non-ionic and cationic agents as have heretofore been used in herbicidal compositions of similar type. Suitable surface active agents are set out, for example, in Searle, U.S. Pat. No. 2,426,417; Todd, U.S. Pat. No. 2,655,447; Jones, U.S. Pat. No. 2,412,510; or Lenher, U.S. Pat. No. 2,139,376. A detailed list of such agents is given in "Detergents & Emulsifiers Annual"—1965 (J. W. McCutcheon, Inc.).

Suitable surface active agents for use in compositions of this invention include amine, alkali and alkaline earth salts of alkylaryl sulfonic acids; amine, alkali and alkaline earth salts of fatty alcohol sulfates; amine, alkali and alkaline earth salts of lignin sulfonic acids; dialkyl esters of alkali metal sulfosuccinates; fatty acid esters of amine, alkali and alkaline earth isothionates or taurates; amine, alkali and alkaline earth salts of polymerized alkyl naphthaline sulfonic acids; methylated or hydroxyethylated cellulose and polyvinyl alcohols. Other suitable surfactants include polyethylene glycol esters with fatty acids and rosin acids; polyethylene glycol ethers with alkylated phenols or with long chain aliphatic alcohols; polyethylene glycol ethers with sorbitan fatty acid esters; polyoxyethylene thio ethers; condensates of mixed polypropylene oxide and polyethylene oxide; and long chain quaternary ammonium compounds. Anionic and non-ionic agents are preferred.

Preferred wetting agents are sodium alkylnaphthalene sulfonates; sodium dioctylsulfosuccinate; sodium dodecylbenzene sulfonates; ethylene oxide condensates with alkylated phenols such as octyl, nonyl or dodecylphenol; sodium lauryl sulfate; and trimethylnonyl polyethylene glycol.

Preferred dispersing agents are sodium, calcium and magnesium ligninsulfonates; low viscosity methyl cellulose; polymerized sodium alkylnaphthalene sulfonates; sodium N-oleyl or N-lauryl isothionates; sodium N-methyl-N-oleyl taurate and sodium dodecyldiphenyloxide disulfonate.

Preferred emulsifying agents are ethylene oxide adducts to lauric, oleic, stearic and palmitic acid esters of sorbitol; polyethylene glycol esters with lauric, oleic, stearic, palmitic and rosin acids; oil soluble alkylaryl sulfonates; oil soluble polyoxyethylene ethers with octyl-, nonyl- and dodecylphenol; polyoxyethylene adducts of long-chain mercaptans; and mixtures of these surfactants.

Powdered and coarse particulate formulations of this invention are commonly prepared by extension of mixtures of active and surfactant with solid diluents. These diluents are added to control the active ingredient content at a constant percentage, to aid in particle size reduction, to reduce caking tendencies, to improve flow characteristics or to grossly extend the active ingredient as in dust or pellet formulations so that low levels of active ingredient can be conveniently applied to soil or foliage. Any one or all of these objectives may be of importance in any given composition.

Solid diluents can be inorganic, such as clays, silica, talcs, synthetic silicates, phosphate rock, pyrophyllite, calcite and vermiculite, or they can be organic, such as tobacco dust, ground corn cob, shell flours or wood flours. Suitable diluents for wettable powders include kaolin clays, montmorillonite clays, diatomaceous silica, attapulgite clays, precipitated forms of calcium carbonate, synthetic silica and synthetic calcium, magnesium and aluminum silicates. For dust preparations, suitable diluents include pyrophyllite, talc, ground phosphate rock, ground limestone and tobacco dust. For granular or pellet compositions, suitable diluents are coarse grinds of corn cob or nut shells, granular attapulgite, granular expanded vermiculite, swelling or non-swelling montmorillonite clays, kaolin clays and ball clays.

Preferred diluents for wettable powders are finely ground kaolin, attapulgite, non-swelling montmorillonite and diatomaceous silica. Other preferred diluents for wettable powders are extremely fine synthetic silica and calcium, aluminum or magnesium silicates. Preferred diluents for dusts are micaceous talc and pyrophyllite. Preferred diluents for preformed granules are coarse-ground corn cob; granular, expanded vermiculite; and granular attaclay. Preferred diluents for extruded pellets or moist granulated and dried products are swelling and non-swelling montmorillonites and kaolin clays.

Other formulating components include liquid extenders such as water to form aqueous suspensions; non-solvent oils to yield liquid, emulsifiable suspensions; and solvent-type organic liquids to yield homogeneous, emulsifiable oils. In general, the compounds of this invention have very low solubility in water-immiscible solvents so that true emulsions in a solvent oil are impractically low in concentration. Solutions in highly polar solvents such as dimethylformamide, dimethylsulfoxide or isophorone, however, can be combined with surfactants to give homogeneous solutions which emulsify momentarily in water, followed by diffusion loss of the solvent into the water leaving a fine-particled, solid dispersion of the active component.

Higher solubility in oils of low polarity can also be obtained by reacting the compounds of this invention with oil soluble sulfonic acids such as dodecylbenzenesulfonic acid to form addition compounds which possess good oil solubility. Combinations of active ingredient, dodecylbenzenesulfonic acid and an oil such as xylene can then be made emulsifiable by the addition of excess sulfonic acid or an oil soluble salt thereof. However, upon emulsification in water, the addition compound commonly disintegrates, leaving the active triazine as a solid, dispersed phase. Compositions solubilized in oil by organic sulfonic acids have greater utility when extended with herbicidal oils rather than water and then applied post-emergence to undesired foliage.

As with dodecylbenzenesulfonic acid, salts with other acids, both organic and inorganic, can be made from compounds of this invention. Of particular interest are salts with herbicidal acids, such as 2,3,6-trichlorobenzoic acid
2,3,5,6-tetrachlorobenzoic acid
2-methoxy-3,5,6-trichlorobenzoic acid
2-methoxy-3,6-dichlorobenzoic acid
3-amino-2,5-dichlorobenzoic acid
3-nitro-2,5-dichlorobenzoic acid
2-methyl-3,6-dichlorobenzoic acid
2,4-dichlorophenoxyacetic acid
2,4,5-trichlorophenoxyacetic acid
(2-methyl-4-chlorophenoxy)acetic acid
2-(2,4,5-trichlorophenoxy)propionic acid
4-(2,4-dichlorophenoxy)butyric acid
4-(2-methyl-4-chlorophenoxy)butyric acid
trichloroacetic acid
2,2-dichloropropionic acid
dimethylarsinic acid
3,6-endohexahydrophthalic acid.

Compositions suitable for field application will usually contain ingredients within the ranges indicated below, although departures from these levels may be desirable for applications with particular equipment or for treatment of particular crops. All percentages are by weight unless otherwise indicated.

Wettable powder concentrates will contain from about 85 to about 98% active ingredient, from 0 to about 14.5% solid diluent and from about 0.5 to about 5% surfactant. Wettable powders will contain from about 20 to about 95% active ingredient, from about 0.5 to about 40% surfactant and from about 4.5 to about 79.5% solid diluents. Preferably wettable powders will contain from about 45 to about 85% active ingredient, from about 0.5 to about 10% surfactant and from about 5.0 to about 54.5% solid diluents. Dusts will contain from about 0.5 to about 25% active ingredients, from 0 to about 5% surfactant and from about 70 to about 99.5% solid carrier diluent.

Aqueous suspensions will contain from about 10 to about 50% active ingredient, from about 0.5 to about 20% dispersing agents and from about 0.2 to about 10% of clays or other suspending agents, the remainder being water. Non-aqueous liquid concentrate compositions will contain from about 5 to 35% active ingredient and from about 0.5 to about 25% surface active agent, the remainder being organic liquid carrier.

Granules or pellets will contain from about 0.5 to about 35% active ingredient, from 0 to about 15% surfactant, from 0 to about 15% inorganic salt, from 0 to about 15% non-volatile binder and from 40 to 99.5% solid carrier or diluent.

In addition to the above-mentioned components, it is often advantageous to incorporate into the compositions of this invention other agents which impart corrosion inhibition, bacterial control, pH control, color, binding properties and the like, or which serve as suspending agents, grinding aids and the like.

The compositions described above are prepared by methods generally used for the preparation of pesticidal compositions of similar type. The solid compositions, with the exception of granules, are prepared in a blending operation which will usually include passage through an attrition mill such as a hammer mill or a fluid energy mill followed by reblending to assure homogeneity.

Solutions are prepared by simple stirring of the combined ingredients. Aqueous and oil suspensions are prepared by ball milling or sand grinding a mixture of the ingredients to produce a slurry of finely divided particles.

Granules are prepared by different procedures. Preformed, absorptive granules are sprayed with a solution of the active ingredient and adjuvants, or with a mixture of the active ingredient and adjuvants which is warmed as needed to produce a free-flowing liquid. Alternatively, the active ingredient and adjuvants are mixed with sufficient liquid to permit the extrusion of pellets or the formation of granules by tumbling.

APPLICATION

In practicing the methods of this invention, one or more compound of Formula (1) is applied to an area to be treated in an amount sufficient to exert the desired herbicidal action. The amount needed to exert the desired herbicidal action is referred to herein as the "herbicidal amount." The term "controlling" as used herein is intended to include killing, inactivating or otherwise inhibiting or retarding the growth of undesired vegetation.

It will be appreciated that the herbicidal amount will vary with the particular weed pest involved, plant density, the application method, prevailing weather conditions, nature of the soil, the desired result such as soil sterilization or control of weeds in crops, the herbicidal activity of the particular active ingredient used, etc. Since many factors are involved, it is not possible to indicate generally one rate of application suitable for all situations. However, effective resolution of these factors in determining the herbicidal amount in a given situation is well within the ability of persons of ordinary skill in the art. Generally suitable ranges of application rates for particular methods and purposes are set forth below.

At rates of 5 to 60 kilograms per hectare the compounds of this invention are useful as general soil sterilants in areas such as railway right-of-ways, truck farms, etc. where complete suppression of vegetative growth is desired.

At application rates of from 2 to 10 kilograms per hectare, these compounds are useful for selective weed control in various crops, e.g., sugarcane, asparagus, and gladiolus.

For the season-long control of cattails (Typha spp.), Maiden Cane (*Phragmites communis*), burreed (Sparganium spp.), rush (Juncus spp.), arrow head (Sagittaria spp.), water primrose (Jussiaea spp.) and smartweed (Persicana spp.) and other unwanted plants growing along the edges of flooded areas, a compound of Formula (1), incorporated into a convenient composition, is applied at a rate of from about 15 to about 30 kilograms per hectare.

Aqueous dispersions are applied at a rate of from about 5 to about 30 kilograms of active ingredient per hectare to emergant aquatic vegetation such as American lotus (Nelumbo spp.), spatterdock (*Nuphar advena*), white water lily (Nymphaea spp.), smartweed (Polygonum spp.) and water lettuce (*Pistia stratiortes*). Such treatment results in control of the undesired vegetation for one-half the growing season. Retreatment with a like amount results in control for the remainder of the season.

In order that this invention can be better understood the following examples are given in addition to the examples already given above. These examples illustrate the preparation of representative 4-amino-2,3-dihydro-3-thiono-as-triazin-5(4H)-one intermediates (Examples 1 through 16), the preparation of representative compounds of Formula (1) (Examples 17 through 66), and typical herbicidal compositions, methods for their preparation, herbicidal applications and results obtained (Examples 67 through 126). It is understood that all percentages are by weight unless otherwise indicated.

EXAMPLE 1

Synthesis of 4-amino-2,3-dihydro-3-thiono-as-triazin-5(4H)-one

A solution of 22 parts glyoxylic acid in 22 parts water is slowly added to a hot, stirred solution of 32 parts thiocarbohydrazide in 350 parts water. The resulting mixture is refluxed until no further precipitate is formed. Upon cooling, essentially pure 4-amino-2,3-dihydro-3-thiono-as-triazin-5(4H)-one having a melting point of 211°–215° C. is obtained by filtration.

EXAMPLES 2-16

The following intermediates are prepared in the manner of the 4-amino-2,3-dihydro-2-thiono-as-triazin-5(4H)-one of Example 1 by substituting equivalent molar amounts of the indicated starting materials for glyoxylic and thiocarbohydrazide used in Example 1.

| Ex. | Starting Materials | Product |
|---|---|---|
| 2 | phenyl glyoxylic acid and thiocarbohydrazide | 4-amino-2,3-dihydro-6-phenyl-3-thiono-as-triazin-5(4H)-one |
| 3 | 2-methoxy-4-methylphenyl glyoxylic acid and thiocarbohydrazide | 4-amino-2,3-dihydro-6-(2-methoxy-4-methylphenyl)-3-thiono-as-triazin-5(4H)-one |
| 4 | 2-mercapto-3-phenyl acrylic acid and thiocarbohydrazide | 4-amino-2,3-dihydro-6-benzyl-3-thiono-as-triazin-5(4H)-one |
| 5 | 2-mercapto-3-(o-fluorophenyl) acrylic acid and thiocarbohydrazide | 4-amino-2,3-dihydro-6-(o-fluorobenzyl)-3-thiono-as-triazin-5(4H)-one |
| 6 | 2-mercapto-3-(3,4-dichlorophenyl) acrylic acid and thiocarbohydrazide | 4-amino-2,3-dihydro-6-(3,4-dichlorobenzyl)-3-thiono-as-triazin-5(4H)-one |
| 7 | pyruvic acid and thiocarbohydrazide | 4-amino-2,3-dihydro-6-methyl-3-thiono-as-triazin-5(4H)-one |
| 8 | p-methoxyphenyl glyoxylic acid and thiocarbohydrazide | 4-amino-2,3-dihydro-6-(p-methoxyphenyl)-3-thiono-as-triazin-5(4H)-one |
| 9 | 2-mercapto-3-(o-nitrophenyl) acrylic acid and thiocarbohydrazide | 4-amino-2,3-dihydro-6-(o-nitrobenzyl)-3-thiono-as-triazin-5(4H)-one |
| 10 | glyoxylic acid and 1,1-dimethylthiocarbohydrazide | 4-dimethylamino-2,3-dihydro-3-thiono-as-triazin-5(4H)-one |
| 11 | 1-naphthyl glyoxylic acid and thiocarbohydrazide | 4-amino-2,3-dihydro-6-(1-naphthyl)-3-thiono-as-triazin-5(4H)-one |
| 12 | 4-isopropylphenyl glyoxylic acid and thiocarbohydrazide | 4-amino-2,3-dihydro-6-(4-isopropylphenyl)-3-thiono-as-triazin-5(4H)-one |
| 13 | 2-mercapto-3-(o-methoxyphenyl)-acrylic acid and thiocarbohydrazide | 4-amino-2,3-dihydro-6-(o-methoxybenzyl)-3-thiono-as-triazin-5(4H)-one |
| 14 | 3-(p-isopropoxyphenyl)-2-mercaptoacrylic acid and 1,1-dimethylthiocarbohydrazide | 4-(dimethylamino)-2,3-dihydro-6-(p-isopropoxybenzyl)-3-thiono-as-triazin-5(4H)-one |
| 15 | 3-(p-cyanophenyl)-2-mercaptoacrylic acid and thiocarbohydrazide | 4-amino-6-(p-cyanobenzyl)-2,3-dihydro-3-thiono-as-triazin-5(4H)-one |
| 16 | 3-cumenyl-2-mercaptoacrylic acid and thiocarbohydrazide | 4-amino-2,3-dihydro-6-(p-isopropylbenzyl)-3-thiono-as-triazin-5(4H)-one |

EXAMPLE 17

4-amino-2,3-dihydro-6-methyl-3-benzylthio-as-triazin-5(4H)-one 6.5 Parts by weight of 4-amino-2,3-dihydro-6-methyl-3-thiono-as-triazin-5(4H)-one is added to a solution of 2.3 parts by weight of sodium methoxide in 50 parts by volume of methanol. After a few minutes 5.2 parts by weight of benzylchloride is added and the resulting mixture is stirred over night at room temperature. The solvent is removed under vacuum and the residue is washed with water to give 4.5 parts of 4-amino-3-benzylthio-6-methyl-as-triazin-5(4H)-one.

EXAMPLES 18–66

The following compounds are prepared in the manner of 4-amino-3-benzylthio-6-methyl-as-triazin-5(4H)-one of Example 17 by substituting equivalent molar amounts of the indicated starting materials for the 4-amino-2,3-dihydro-6-methyl-3-thiono-as-triazin-5(4H)-one and benzylchloride used in Example 7:

| Ex. | Starting Materials | Product |
|---|---|---|
| 18 | 4-amino-2,3-dihydro-6-phenyl-3-thiono-as-triazin-5(4H)-one and methyl iodide | 4-amino-3-methylthio-6-phenyl-as-triazin-5(4H)-one |
| 19 | 4-amino-2,3-dihydro-6-(4-nitrophenyl)-3-thiono-as-triazin-5(4H)-one and ethyl bromoacetate | 4-amino-3-ethoxycarbonylmethylthio-6-(4-nitrophenyl)-as-triazin-5(4H)-one |
| 20 | 4-amino-6-(3,4-dichlorophenyl)-2,3-dihydro-3-thiono-as-triazin-5(4H)-one and allyl bromide | 3-allylthio-4-amino-6-(3,4-dichlorophenyl)-as-triazin-5(4H)-one |
| 21 | 4-amino-2,3-dihydro-6-(1-naphthyl)-3-thiono-as-triazin-5(4H)-one and n-butyl bromide | 4-amino-3-(n-butylthio)-6-(1-naphthyl)-as-triazin-5(4H)-one |
| 22 | 4-amino-2,3-dihydro-6-(m-tolyl)-3-thiono-as-triazin-5(4H)-one and n-butyl iodide | 4-amino-3-(n-butylthio)-6-(m-tolyl)-as-triazin-5(4H)-one |
| 23 | 4-amino-2,3-dihydro-6-phenyl-3-thiono-as-triazin-5(4H)-one and methyl bromo propionate | 4-amino-3-(2-methoxycarbonylethylthio)-6-phenyl-as-triazin-5(4H)-one |
| 24 | 4-amino-2,3-dihydro-6-(n-octyl)-3-thiono-as-triazin-5(4H)-one and methyl iodide | 4-amino-3-methylthio-6-(n-octyl)-as-triazin-5(4H)-one |
| 25 | 4-amino-2,3-dihydro-6-methyl-3-thiono-as-triazin-5(4H)-one and ethyl bromoacetate | 4-amino-3-ethoxycarbonylmethylthio-6-methyl-as-triazin-5(4H)-one |
| 26 | 4-amino-2,3-dihydro-6-(n-octyl)-3-thiono-as-triazin-5(4H)-one and n-butyl iodide | 4-amino-3-(n-butylthio)-6-(n-octyl)-as-triazin-5(4H)-one |
| 27 | 4-amino-2,3-dihydro-2-thiono-as-triazin-5(4H)-one and methyl iodide | 4-amino-3-methylthio-as-triazin-5(4H)-one |
| 28 | 4-amino-2,3-dihydro-2-thiono-as-triazin-5(4H)-one and n-butyl iodide | 4-amino-3-(n-butylthio)-as-triazin-5(4H)-one |
| 29 | 4-amino-2,3-dihydro-2-thiono-as-triazin-5(4H)-one and sec-butyl bromide | 4-amino-3-(sec-butylthio)-as-triazin-5(4H)-one |
| 30 | 4-amino-2,3-dihydro-2-thiono-as-triazin-5(4H)-one and isobutylbromide | 4-amino-3-(isobutylthio)-as-triazine-5(4H)-one |
| 31 | 4-amino-2,3-dihydro-2-thiono-as-triazin-5(4H)-one and methyl bromoacetate | 4-amino-3-methoxycarbonylmethylthio-as-triazin-5(4H)-one |
| 32 | 2,3-dihydro-6-(1-naphthyl)-4-pyrrolidino-3-thiono-as-triazin-5(4H)-one and methyl iodide | 3-methylthio-4-pyrrolidino-6-(1-naphthyl)-as-triazin-5(4H)-one |
| 33 | 4-methylamino-2,3-dihydro-6-(2-naphthyl)-3-thiono-as-triazin-5(4H)-one and isobutyl iodide | 3-isobutylthio-4-methylamino-6-(2-naphthyl)-as-triazin-5(4H)-one |
| 34 | 4-amino-6-(2-fluorophenyl)-2,3-dihydro-3-thiono-as-triazin-5(4H)-one and methyl iodide | 4-amino-6-(2-fluorophenyl)-3-methylthio-as-triazin-5(4H)-one |
| 35 | 4-amino-6-(m-chlorophenyl)-2,3-dihydro-3-thiono-as-triazin-5(4H)-one and sec-butyl iodide | 4-amino-3-(sec-butylthio)-6-(m-chlorophenyl)-as-triazin-5(4H)-one |
| 36 | 4-amino-6-(p-bromophenyl)-3-thiono-as-triazin-5(4H)-one and ethyl bromoacetate | 4-amino-3-ethoxycarbonylmethylthio-6-(p-bromophenyl)-as-triazin-5(4H)-one |
| 37 | 4-amino-2,3-dihydro-6-(p-iodophenyl)-3-thiono-as-triazin-5(4H)-one and ethyl iodide | 4-amino-3-ethylthio-6-(p-iodophenyl)-as-triazin-5(4H)-one |
| 38 | 4-amino-2,3-dihydro-6-(p-isopropylphenyl)-3-thiono-as-triazin-5(4H)-one and methyl iodide | 4-amino-6-(p-isopropylphenyl)-3-methylthio-as-triazin-5(4H)-one |
| 39 | 4-amino-2,3-dihydro-6-(2,4-xylyl)-3-thiono-as-triazin-5(4H)-one and sec-butyl iodide | 4-amino-3-(sec-butylthio)-6-(2,4-xylyl)-as-triazin-5(4H)-one |
| 40 | 4-dimethylamino-2,3-dihydro-6-(2,4-xylyl)-3-thiono-as-triazin-5(4H)-one and ethyl bromoacetate | 4-dimethylamino-3-ethoxycarbonylmethylthio-6-(2,4-xylyl)-as-triazin-5(4H)-one |
| 41 | 4-amino-2,3-dihydro-6-phenyl-3-thiono-as-triazin-5(4H)-one and ethyl bromoacetate | 4-amino-3-ethoxycarbonylmethylthio-6-phenyl-as-triazin-5(4H)-one |
| 42 | 4-amino-6-(4-chloro-3-nitrophenyl)-2,3-dihydro-3-thiono-as-triazin-5(4H)-one and ethyl iodide | 4-amino-3-ethylthio-6-(4-chloro-3-nitrophenyl)-as-triazin-5(4H)-one |
| 43 | 4-amino-6-(4-chloro-3-cyanophenyl-2,3-dihydro-3-thiono-as-triazin-5(4H)-one and isobutyl bromide | 4-amino-6-(4-chloro-3-cyanophenyl)-3-isobutylthio-as-triazin-5(4H)-one |
| 44 | 4-amino-6-(2,4-dimethoxyphenyl)-2,3-dihydro-3-thiono-as-triazin-5(4H)-one and methyl bromoacetate | 4-amino-3-methoxycarbonylmethylthio-6-(2,4-dimethoxyphenyl)-as-triazin-5(4H)-one |
| 45 | 4-amino-2,3-dihydro-6-(4-methoxy-o-tolyl)-3-thiono-as-triazin-5(4H)-one and n-propyl chloroformate | 4-amino-6-(4-methoxy-o-tolyl)-3-n-propoxycarbonylthio-as-triazin-5(4H)-one |
| 46 | 4-amino-2,3-dihydro-6-(2-methoxy-p-tolyl)-3-thiono-as-triazin-5(4H)-one and sec-butyl iodide | 4-amino-3-(sec-butylthio)-6-(2-methoxy-p-tolyl)-as-triazin-5(4H)-one |
| 47 | 4-amino-2,3-dihydro-6-(p-n-propoxyphenyl)-3-thiono-as-triazin-5(4H)-one and methyl iodide | 4-amino-3-methylthio-6-(p-n-propoxyphenyl)-as-triazin-5(4H)-one |
| 48 | 4-amino-2,3-dihydro-6-(p-isopropoxyphenyl)-3-thiono-as-triazin-5(4H)-one and methyl iodide | 4-amino-3-methylthio-6-(p-isopropoxyphenyl)-as-triazin-5(4H)-one |
| 49 | 4-(n-butylamino)-6-(p-cyanophenyl)-2,3-dihydro-3-thiono-as-triazin-5(4H)-one and methyl iodide | 4-(n-butylamino)-6-(p-cyanophenyl)-3-methylthio-as-triazin-5(4H)-one |
| 50 | 4-(sec-butylamino)-6-(p-cyanophenyl)-2,3-dihydro-3-thiono-as-triazin-5(4H)-one and methyl iodide | 4-(sec-butylamino)-6-(p-cyanophenyl)-3-methylthio-as-triazin-5(4H)-one |
| 51 | 2,3-dihydro-6-(p-methoxyphenyl)-4-morpholino-3-thiono-as-triazin-5(4H)-one and ethyl iodide | 3-ethylthio-6-(p-methoxyphenyl)-4-morpholino-as-triazin-5(4H)-one |
| 52 | 2,3-dihydro-6-(p-fluorophenyl)-4-piperidino-3-thiono-as-triazin-5(4H)-one and methyl iodide | 6-(p-fluorophenyl)-3-methylthio-4-piperidino-as-triazin-5(4H)-one |
| 53 | 4-anilino-6-(p-cyanophenyl)-2,3-dihydro-3-thiono-as-triazin-5(4H)-one and methyl iodide | 4-anilino-6-(p-cyanophenyl)-3-methylthio-as-triazin-5(4H)-one |
| 54 | 4-amino-2,3-dihydro-6-(p-tolyl)-3-thiono-as-triazin-5(4H)-one and methyl chloroformate | 4-amino-3-methoxycarbonylthio-6-(p-tolyl)-as-triazin-5(4H)-one |
| 55 | 4-amino-2,3-dihydro-6-benzyl-3-thiono-as-triazin-5(4H)-one and methyl iodide | 4-amino-6-benzyl-3-methylthio-as-triazin-5(4H)-one |
| 56 | 4-amino-2,3-dihydro-6-(o-nitrobenzyl)-3-thiono-as- | 4-amino-3-methylthio-6-(o-nitrobenzyl)-as- |

| Ex. | Starting Materials | Product |
|---|---|---|
| | triazin-5(4H)-one and methyl iodide | triazin-5(4H)-one |
| 57 | 4-amino-2,3-dihydro-6-(3,4-dichlorobenzyl)-3-thiono-as-triazin-5(4H)-one and methyl iodide | 4-amino-6-(3,4-dichlorobenzyl)-3-methylthio-as-triazin-5(4H)-one |
| 58 | 4-amino-2,3-dihydro-6-(p-methylbenzyl)-3-thiono-as-triazin-5(4H)-one and methyl iodide | 4-amino-6-(p-methylbenzyl)-3-methylthio-as-triazin-5(4H)-one |
| 59 | 4-amino-2,3-dihydro-6-(p-methoxyphenyl)-3-thiono-as-triazin-5(4H)-one and methyl iodide | 4-amino-3-methylthio-6-(p-methoxyphenyl)-as-triazin-5(4H)-one |
| 60 | 4-amino-2,3-dihydro-6-(2-methoxy-4-methylphenyl)-3-thiono-as-triazin-5(4H)-one and methyl iodide | 4-amino-3-methylthio-6-(2-methoxy-4-methylphenyl)-as-triazin-5(4H)-one |
| 61 | 4-amino-2,3-dihydro-6-(4-bromophenyl)-3-thiono-as-triazin-5(4H)-one and methyl iodide | 4-amino-3-methylthio-6-(4-bromophenyl)-as-triazin-5(4H)-one |
| 62 | 4-amino-2,3-dihydro-6-(o-methoxybenzyl)-3-thiono-as-triazin-5(4H)-one and methyl iodide | 4-amino-6-(o-methoxybenzyl)-3-methylthio-as-triazin-5(4H)-one |
| 63 | 4-(dimethylamino)-2,3-dihydro-6-(p-isopropoxybenzyl)-3-thiono-as-triazin-5(4H)-one and ethyl iodide | 4-(dimethylamino)-3-ethylthio-6-(p-isopropoxybenzyl)-as-triazin-5(4H)-one |
| 64 | 4-amino-2,3-dihydro-6-propyl-3-thiono-as-triazin-5(4H)-one and methyl iodide | 4-amino-3-methylthio-6-propyl-as-triazin-5(4H)-one |
| 65 | 4-amino-6-(p-cyanobenzyl)-2,3-dihydro-3-thiono-as-triazin-5(4H)-one and methyl iodide | 4-amino-6-(p-cyanobenzyl)-3-methylthio-as-triazin-5(4H)-one |
| 66 | 4-amino-2,3-dihydro-6-(p-isopropylbenzyl)-3-thiono-as-triazin-5(4H)-one and methyl iodide | 4-amino-6-(p-isopropylbenzyl)-3-methylthio-as-triazin-5(4H)-one |

EXAMPLE 67

| Wettable Powder: | Percent |
|---|---|
| 4-amino-3-methylthio-6-(2-nitrobenzyl)-as-triazin-5(4H)-one | 80 |
| sodium alkylnaphthalene sulfonate | 2 |
| partially desulfonated sodium lignin sulfonate | 2 |
| kaolin clay | 16 |

The above components are blended together and micropulverized until substantially all particles are less than 50 microns. The resulting powder wets and disperses readily in water.

Sixty kilograms of the above composition is extended with 500 liters of water. The resultant suspension is uniformly sprayed, under constant agitation, on a one-hectare section of land which is infested with quackgrass. As a result of this treatment the quackgrass is killed.

EXAMPLE 68

| Wettable Powder Concentrate: | Percent |
|---|---|
| 4-amino-3-methylthio-6-phenyl-as-triazin-5(4H)-one | 95.0 |
| dioctylsodium sulfosuccinate | 1.5 |
| low viscosity methyl cellulose | 0.5 |
| synthetic fine silica | 3.0 |

The above components are combined in the manner described in Example 67 resulting in a high strength wettable powder.

Four kilograms of this powder suspended in 400 liters of water is applied as a pre-emergence treatment to one hectare of ratooned sugarcane using a tractor-mounted sprayer. Excellent control of crabgrass, ragweed, wild pepper and goat weed is thereby obtained. The cane emerges normally and results in a good crop.

EXAMPLE 69

| Wettable Powder: | Percent |
|---|---|
| 4-amino-3-methylthio-6-(2-methoxy-p-tolyl)-as-triazin-5(4H)-one | 50.0 |
| dodecylphenol adduct with polyethylene oxide | 1.0 |
| diatomaceous silica | 10.0 |
| kaolin clay | 35.0 |
| calcium lignin sulfonate | 4.0 |

The active component is charged into a blender and the liquid dodecylphenol-polyethylene oxide adduct is sprayed upon it with tumbling. The remaining components are then added and blending is continued to uniformity. The mixture is then micropulverized until substantially all particles are less than 50 microns.

Six kilograms of the resulting wettable powder suspended in 250 liters of water is applied as a pre-emergence treatment to a one-hectare test plot within an asparagus field having light textured soil. This treatment provides excellent control of barnyard grass, green foxtail and lambsquarters and the asparagus, thus freed from weed competition, exhibits vigorous growth and produces an excellent crop. In untreated areas of the field the asparagus grows poorly because of competition with thick stands of barnyard grass, green foxtail and lambsquarters.

EXAMPLE 70

| Aqueous Suspension: | Percent |
|---|---|
| 4-amino-3-methylthio-6-(p-isopropylphenyl)-as-triazin-5(4H)-one | 30.0 |
| calcium, magnesium lignin sulfonate | 15.0 |
| sodium pentachlorophenate | 0.7 |
| hydrated attapulgite | 1.8 |
| anhydrous sodium carbonate | 2.0 |
| water | 50.5 |

The above components are first mixed together in a slurry tank, then passed through a sand mill to yield a homogeneous, stable aqueous suspension in which the active material is substantially all less than 5 microns.

Thirty-five kilograms of the composition is suspended in 700 liters of water and applied at the outset of the growing season to a one-hectare area of a railroad yard which is heavily infested with barnyard grass, annual blue grass, crabgrass, pigweed and annual smartweed. The treatment provides season-long control of all of the above-mentioned weedy vegetation. In subsequent years as little as 5 kilograms per hectare of the above formulation is sufficient to maintain control of weedy vegetation.

EXAMPLE 71

Fifty kilograms of the formulation of Example 70 in 200 liters of water is sprayed onto the hectare of emergent aquatic vegetation including American lotus, white water lily, spatterdock, smartweed and water lettuce. This treatment effectively controls the growth of these aquatic weeds.

EXAMPLE 72

| Granules or Pellets: | Percent |
| --- | --- |
| 4-amino-3-ethoxycarbonylmethylthio-6-phenyl-as-triazin-5(4H)-one | 25 |
| non-swelling Ca, Mg bentonite | 64 |
| anhydrous sodium sulfate | 10 |
| sodium alkylnaphthalene sulfonate | 1 |

The above components are blended and micropulverized and then mixed in a pug mill with about 15 to 17% by weight water and extruded through die holes of approximately three millimeters diameter. The extrusions are dried and granulated to form particles having diameters ranging from about 0.25 to 1.5 millimeters. Alternatively the extrusions are cut with a knife as they emerge, to form 3 mm. by 3 mm. pellets which are then dried.

These granules or pellets are applied manually, at a rate of 25 grams of active ingredient per square meter to an area at the base of a cluster of highway signs. The area consists of sandy soil and usually supports a heavy infestation of unsightly nutsedge. The treatment is watered into the soil. Good control of nutsedge is obtained.

EXAMPLE 73

The pelleted formulation of Example 72 is applied at a rate which provides 30 kilograms of active ingredient per hectare to flooded areas infested with water smartweed, arrowhead, maidencane, water primrose and cattails. Good control of these weeds is obtained.

EXAMPLE 74

| Light Granules: | Percent |
| --- | --- |
| Wettable Powder Concentrate of Example 68 | 10.5 |
| propylene glycol | 10 |
| granular #4 expanded vermiculite | 79.5 |

The wettable powder concentrate is tumbled briefly with the vermiculite and the mix is then sprayed with the propylene glycol to prevent subsequent segregation.

The resulting granules are then applied at the rate which provides 2 kilograms of active ingredient per hectare on a bed of gladioluses planted two days previously. The material is washed into the soil by means of sprinkler irrigation. Excellent control of weedy plants such as crabgrass, yellow foxtail, lambsquarters and pigweed is obtained for a period of seven weeks. The gladioluses grow well and produce good yields of corms and cut flowers.

EXAMPLE 75

| Emulsifiable Liquid: | Percent |
| --- | --- |
| 4-amino-3-methylthio-6-(4-bromophenyl)-as-triazin-5(4H)-one | 25 |
| low viscosity white mineral oil | 65 |
| blend of alkyl phenol polyethylene glycol and oil soluble alkyl benzene sulfonate | 10 |

The above components are blended and then sand milled to give an oil suspension of the active ingredient. When mixed with water a three phase system results in which the oil is emulsified and the active ingredient is dispersed in part in the oil and in part in the water phase.

The above composition is extended with water and applied at the rate which provides 25 kilograms of active ingredient in 700 liters of water per hectare to weed-infested sandy areas around an oil storage tank. The treatment provides season-long control of a mixed weed population which normally occurs in this area, including quackgrass, green and yellow foxtail, barnyard grass, smartweed, black-eyed susan, and shepherd's purse.

EXAMPLES 76-101

The following compounds are substituted individually in a like percent by weight for the 4-amino-3-methylthio-6-(2-methoxy-p-tolyl)-as-triazin-5(4H)-one in Example 69 and are formulated and applied in a like manner with like results being obtained:

| Example | Compound |
| --- | --- |
| 76 | 4-amino-2,3-dihydro-6-methyl-3-benzylthio-as-triazin-5(4H)-one |
| 77 | 4-amino-3-methylthio-6-phenyl-as triazin-5(4H)-one |
| 78 | 4-amino-3-ethoxycarbonylmethylthio-6-(4-nitrophenyl)-as-triazin-5(4H)-one |
| 79 | 3-allylthio-4-amino-6-(3,4-dichlorophenyl)-as-triazin-5(4H)-one |
| 80 | 4-amino-3-(n-butylthio)-6-(1-naphthyl)-as-triazin-5(4H)-one |
| 81 | 4-amino-3-(n-butylthio)-6-(m-tolyl)-as-triazin-5(4H)-one |
| 82 | 4-amino-3-(2-methoxycarbonylethylthio)-6-phenyl-as-triazin-5(4H)-one |
| 83 | 4-amino-3-methylthio-6-(n-octyl)-as-triazin-5(4H)-one |
| 84 | 4-amino-3-ethoxycarbonylmethylthio-6-methyl-as-triazin-5(4H)-one |
| 85 | 4-amino-3-(n-butylthio)-6-(n-octyl)-as-triazin-5(4H)-one |
| 86 | 4-amino-3-methylthio-as-triazin-5(4H)-one |
| 87 | 4-amino-3-(n-butylthio)-as-triazin-5(4H)-one |
| 88 | 4-amino-3-(sec-butylthio)-as-triazin-5(4H)-one |
| 89 | 4-amino-3-(isobutylthio)-as-triazin-5(4H)-one |
| 90 | 4-amino-3-methoxycarbonylmethylthio-as-triazin-5(4H)-one |
| 91 | 3-methylthio-4-pyrrolidino-6-(1-naphthyl)-as-triazin-5(4H)-one |
| 92 | 3-isobutylthio-4-methylamino-6-(2-naphthyl)-as-triazin-5(4H)-one |
| 93 | 4-amino-6-(2-fluorophenyl)-3-methylthio-as-triazin-5(4H)-one |
| 94 | 4-amino-3-(sec-butylthio)-6-(m-chlorophenyl)-as-triazin-5(4H)-one |
| 95 | 4-amino-3-ethoxycarbonylmethylthio-6-(p-bromophenyl)-as-triazin-5(4H)-one |

| Example | Compound |
|---|---|
| 96 | 4-amino-3-ethylthio-6-(p-iodophenyl)-as-triazin-5(4H)-one |
| 97 | 4-amino-6-(p-isopropylphenyl)-3-methylthio-as-triazin-5(4H)-one |
| 98 | 4-amino-3-(sec-butylthio)-6-(2,4-xylyl)-as-triazin-5(4H)-one |
| 99 | 4-dimethylamino-3-ethoxycarbonylmethylthio-6-(2,4-xylyl)-as-triazin-5(4H)-one |
| 100 | 4-amino-3-ethoxycarbonylmethylthio-6-phenyl-as-triazin-5(4H)-one |
| 101 | 4-amino-6-(p-methoxyphenyl)-3-methylthio-as-triazin-5(4H)-one |

EXAMPLES 102-126

The following compounds are substituted individually in a like percent by weight for the 4-amino-3-ethoxycarbonylmethylthio-6-phenyl-as-triazin-5(4H)-one in Example 72 and are formulated and applied in a like manner. Like results are obtained:

| Example | Compound |
|---|---|
| 102 | 4-amino-3-ethylthio-6-(4-chloro-3-nitrophenyl)-as-triazin-5(4H)-one |
| 103 | 4-amino-6-(4-chloro-3-cyanophenyl)-3-isobutylthio-as-triazin-5(4H)-one |
| 104 | 4-amino-3-methoxycarbonylmethylthio-6-(2,4-dimethoxyphenyl)-as-triazin-5(4H)-one |
| 105 | 4-amino-6-(4-methoxy-o-tolyl)-3-n-propoxycarbonylthio-as-triazin-5(4H)-one |
| 106 | 4-amino-3-(sec-butylthio)-6-(2-methoxy-p-tolyl)-as-triazin-5(4H)-one |
| 107 | 4-amino-3-methylthio-6-(p-n-propoxyphenyl)-as-triazin-5(4H)-one |
| 108 | 4-amino-3-methylthio-6-(p-isopropoxyphenyl)-as-triazin-5(4H)-one |
| 109 | 4-(n-butylamino)-6-(p-cyanophenyl)-3-methylthio-as-triazin-5(4H)-one |
| 110 | 4-(sec-butylamino)-6-(p-cyanophenyl)-3-methylthio-as-triazin-5(4H)-one |
| 111 | 3-ethylthio-6-(p-methoxyphenyl)-4-morpholino-as-triazin-5(4H)-one |
| 112 | 6-(p-fluorophenyl)-3-methylthio-4-piperidino-as-triazin-5(4H)-one |
| 113 | 4-anilino-6-(p-cyanophenyl)-3-methylthio-as-triazin-5(4H)-one |
| 114 | 4-amino-3-methoxycarbonylthio-6-(p-tolyl)-as-triazin-5(4H)-one |
| 115 | 4-amino-6-benzyl-3-methylthio-as-triazin-5(4H)-one |
| 116 | 4-amino-3-methylthio-6-(o-nitrobenzyl)-as-triazin-5(4H)-one |
| 117 | 4-amino-6-(3,4-dichlorobenzyl)-3-methylthio-as-triazin-5(4H)-one |
| 118 | 4-amino-6-(p-methylbenzyl)-3-methylthio-as-triazin-5(4H)-one |
| 119 | 4-amino-3-methylthio-6-(p-methoxyphenyl)-as-triazin-5(4H)-one |
| 120 | 4-amino-3-methylthio-6-(2-methoxy-4-methylphenyl)-as-triazin-5(4H)-one |
| 121 | 4-amino-3-methylthio-6-(4-bromophenyl)-as-triazin-5(4H)-one |
| 122 | 4-amino-6-(o-methoxybenzyl)-3-methylthio-as-triazin-5(4H)-one |
| 123 | 4-(dimethylamino)-3-ethylthio-6-(p-isopropoxybenzyl)-as-triazin-5(4H)-one |
| 124 | 4-amino-3-methylthio-6-propyl-as-triazin-5(4H)-one |
| 125 | 4-amino-6-(p-cyanobenzyl)-3-methylthio-as-triazin-5(4H)-one |
| 126 | 4-amino-6-(p-isopropylbenzyl)-3-methylthio-as-triazin-5(4H)-one |

I claim:
1. Substituted 1,2,4-triazine-5-one having the formula

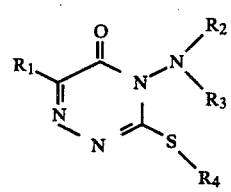

wherein
$R_1$ is hydrogen, alkyl of 1 through 8 carbon atoms, naphthyl, benzyl, phenyl, or

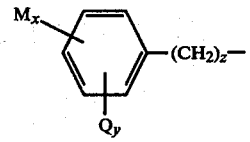

wherein
M and Q are each separately halogen, nitro, cyano, alkyl of 1 through 3 carbon atoms, or alkoxy of 1 through 3 carbon atoms,
x and y are each integers from 0 to 2 provided that the sum of x and y is either 1 or 2, and
z is 0 or 1;
$R_2$ and $R_3$ are each separately hydrogen, alkyl of 1 through 4 carbon atoms, phenyl, or
$R_2$, $R_3$ and the nitrogen atom to which they are bonded taken together form morpholino, piperidino, or pyrrolidino; and
$R_4$ is hydrogen, alkyl of 1 through 4 carbons, benzyl, allyl, carboalkoxy of 2 through 4 carbon atoms, or carboalkoxy alkyl of 3 through 4 carbon atoms,
provided that when $R_4$ is hydrogen or methyl and $R_2$ and $R_3$ are each hydrogen, then $R_1$ is other than methyl or phenyl.

2. Substituted 1,2,4-triazine-5-one according to claim 1 wherein
$R_1$ is alkyl of 1 through 8 carbon atoms, benzyl, phenyl, or

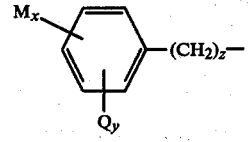

wherein
M and Q are each separately halogen, nitro, cyano, alkyl of 1 through 3 carbon atoms, or alkoxy of 1 through 3 carbon atoms,
x and y are each integers from 0 to 2 provided that the sum of x and y is either 1 or 2; and
z is 0 or 1;
$R_2$ and $R_3$ are each separately hydrogen, or alkyl of 1 through 4 carbon atoms, and R4 is hydrogen, alkyl of 1 through 4 carbon atoms, benzyl, allyl, carboalkoxy of 2 through 4 carbon atoms, or carboalkoxy alkyl of 3 through 4 carbon atoms.

3. Substituted 1,2,4-triazine-5-one according to claim 1 wherein $R_1$ is alkyl of 1 through 8 carbon atoms, benzyl, phenyl, or

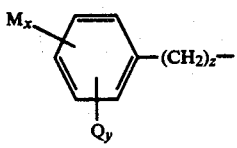

wherein

M and Q are each separately halogen, nitro, cyano, alkyl of 1 through 3 carbon atoms, or alkoxy of 1 through 3 carbon atoms, x and y are each integers from 0 to 2 provided that the sum of x and y is either 1 or 2, and z is 0 or 1;

$R_2$ and $R_3$ are each hydrogen, and $R_4$ is hydrogen, alkyl of 1 through 4 carbon atoms, benzyl, allyl.

4. Substituted 1,2,4-triazine-5-one according to claim 1 wherein $R_1$ is alkyl of 1 through 8 carbon atoms, benzyl, or phenyl, $R_2$ and $R_3$ are each hydrogen, and $R_4$ is alkyl of 1 through 4 carbon atoms or allyl.

5. Substituted 1,2,4-triazine-5-one according to claim 1 wherein $R_1$ is alkyl of 1 through 8 carbon atoms, $R_2$ and $R_3$ are each hydrogen, and $R_4$ is alkyl of 1 through 4 carbon atoms, or allyl.

6. Substituted 1,2,4-triazine-5-one according to claim 5 wherein $R_4$ is methyl or allyl.

* * * * *